United States Patent [19]

Nightingale

[11] Patent Number: 5,033,631
[45] Date of Patent: Jul. 23, 1991

[54] METHOD AND APPARATUS FOR EXPELLING AIR FROM A FLEXIBLE LINER BABY NURSING BOTTLE

[76] Inventor: Harold Nightingale, 305 Terryville Ave., Bristol, Conn. 06010

[21] Appl. No.: 477,244

[22] Filed: Feb. 8, 1990

[51] Int. Cl.⁵ .............................................. A61J 9/00
[52] U.S. Cl. .................................. 215/11.1; 215/11.3; 215/11.6; 222/1; 222/105; 222/326
[58] Field of Search ............... 215/11.1, 11.3, 11.6, 215/11.4; 222/326, 95, 105, 340, 386

[56] References Cited

U.S. PATENT DOCUMENTS

| 950,710 | 3/1910 | Williams | 215/11.1 |
| 1,729,219 | 9/1929 | Kellogg | 222/326 |
| 2,626,730 | 1/1953 | Gabler | 222/326 |
| 3,272,401 | 9/1966 | Fendler et al. | 222/326 |
| 3,648,873 | 3/1972 | Grobbel | 215/11.3 |
| 4,072,249 | 2/1978 | Ekenstam et al. | 222/95 |
| 4,090,646 | 5/1978 | Dubiel et al. | 222/326 |
| 4,131,217 | 12/1978 | Sandegren | 222/326 X |
| 4,176,754 | 12/1979 | Miller | 215/11.3 |
| 4,236,516 | 12/1980 | Nilson | 222/95 X |
| 4,323,176 | 4/1982 | Sartain | 222/326 |
| 4,339,046 | 7/1982 | Coen | 215/11.4 X |
| 4,880,125 | 11/1989 | Le Beau | 215/11.3 |

FOREIGN PATENT DOCUMENTS

| 1010424 | 5/1977 | Canada | 215/11.3 |
| 1288915 | 2/1962 | France | 222/95 |
| 1430276 | 1/1966 | France | 222/95 |
| 461207 | 1/1951 | Italy | 222/326 |
| 203567 | 6/1939 | Switzerland | 222/105 |
| 778124 | 7/1957 | United Kingdom | 222/326 |

Primary Examiner—Sue A. Weaver
Attorney, Agent, or Firm—McCormick, Paulding & Huber

[57] ABSTRACT

A method and related apparatus for expelling air from a flexible liner baby nursing bottle includes an axially elongated connecting rod which is guided and carried by a support bushing having the general size and shape of the lower open end portion of the shell body of the nursing bottle. The support bushing is located intermediate a disk shaped ram portion at one end of the connecting rod and a supporting handle at the opposite end of the connecting rod. The support bushing is inserted into the open end of the shell body and the ram portion is moved axially along a rectilinear path to decrease the volume of the flexible liner and expel air from within the cavity formed by the nipple and the flexible liner through an orifice in the nipple at the upper open end of the shell body. During interruption of the nursing process, the apparatus and nursing bottle are set in an upright position whereby the ram maintains the volume of the flexible liner to that of the volume of liquid in the baby bottle to prevent air from reentering the liner through the orifice in the nipple.

7 Claims, 1 Drawing Sheet

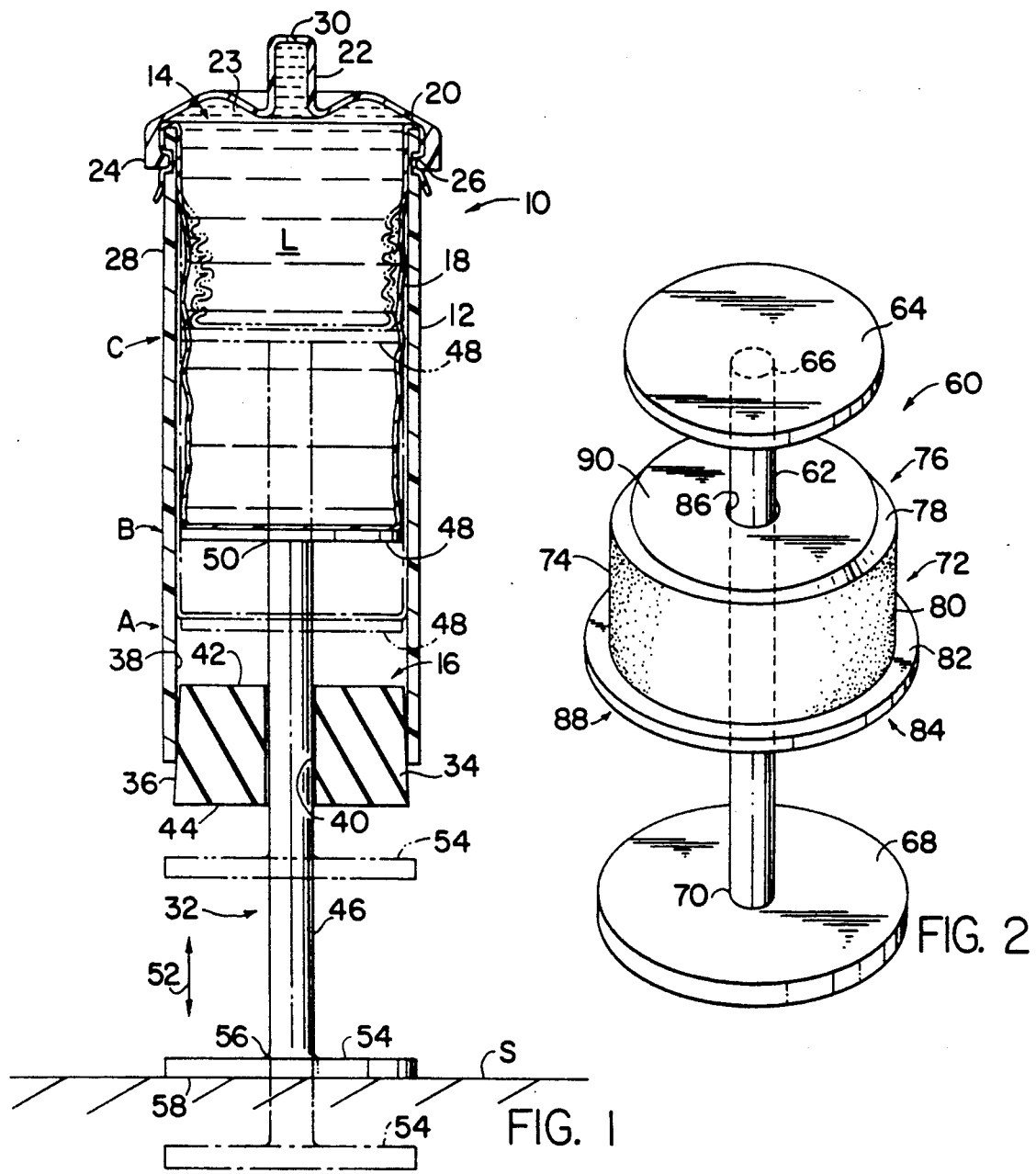

METHOD AND APPARATUS FOR EXPELLING AIR FROM A FLEXIBLE LINER BABY NURSING BOTTLE

BACKGROUND OF THE INVENTION

The present invention relates generally to flexible liner baby nursing bottles of the general type having an open ended shell body and flexible liner and more particularly to apparatus for varying the volume of the liner to expel unwanted air and to prevent reentry of air through the nipple. The invention also relates to a method for using the apparatus to vary the volume of the flexible liner of the baby nursing bottle.

A common problem generally associated with nursing baby bottles is the presence of air in the bottle and which air can be the cause of gas, coughing, or other gastric intestinal disturbances. This problem is generally associated with a conventional baby nursing bottles and has been somewhat solved by the usage of flexible liner baby nursing bottles of the general type in which a flexible liner is supported by a cylindrical, open ended shell body and a nipple which holds the liner to the shell. One such type is commonly known as the "Playtex baby nurser" manufactured by the Playtex Corporation. These nursing baby bottles have become widely used and accepted because the flexible liner decreases in volume as the infant feeds thereby permitting the infant to receive formula or other liquids without sucking in air.

Baby nursing bottles, such as the above-referenced type, initially require that air in the chamber formed by the nipple and the liner cavity be expelled manually prior to the start of feeding. One typical and common method of expelling air is for the user to insert his or her fingers into the open end of the shell body and push on the liner until all of the air is expelled and only liquid remains in the liner and nipple portion. While air may be expelled in this manner for a full bottle, as the amount of liquid in the bottle diminishes the liner must be pushed further into the shell from the open lower end of the shell body until the user's fingers can no longer reach the liner to compress the liner and liquid contained therein to expel any captured air.

Another common problem generally associated with flexible liner baby nursing bottles is the reentry of air into the liner after the bottle has been put aside, particularly in an upright position such as might be the case when the baby is being burped or otherwise attended to. The weight of the liquid in the liner tends to pull the liner downward drawing air into the liner through the nipple. Air may also be drawn into the liner when the baby stops sucking for a period of time since the vacuum created by the sucking is removed.

One attempt to solve the problem of air reentry is the use of a mating cap that contacts or compresses the nipple to form a seal. However, the mating cap seldom works efficiently which allows air to reenter the liner of the baby nursing bottle and requires that a user interrupt the infant feeding to attempt to expel the air once again. Additionally, the mating cap does not solve the problem of expelling air which already exists in the liner, its difficulty and usage during the infant feeding process and must generally be sterilized prior to use since it comes into contact with the nipple of the bottle.

It is desirable therefore to provide apparatus and a related method for use with a flexible liner baby nursing bottle which generally overcomes the problems of expelling air from the bottle described above.

It is a general aim therefore of the present invention to provide a method and apparatus which may be used with a flexible liner baby nursing bottle to vary the volume of the liner containing the formula or the like.

It is another aim of the present invention to provide a method and apparatus for use with a flexible liner baby nursing bottle which expels air from the liner.

It is another aim of the present invention to provide a method and apparatus for use with a flexible liner baby nursing bottle which prevents the reentry of air into the liner when the bottle is set aside during interruption of the nursing process.

It is yet a further aim of the present invention to provide a method and apparatus for use with a flexible liner baby nursing bottle that is inexpensive, easy to use and hygienically safe.

SUMMARY OF THE INVENTION

In accordance with the present invention, apparatus for expelling air from a flexible liner baby nursing bottle is presented and includes a connecting rod which passes axially through a support bushing which has the general shape of and slightly larger peripheral size than the lower open end portion of the shell body carrying the flexible liner. The support bushing has an axial opening for carrying and guiding a connecting rod and is located intermediate a ram and handle each connected at respective opposite ends of the connecting rod. The ram is preferably disk shaped and slightly smaller than the inner cross sectional area of the shell body. The handle portion is also preferably disk shaped and serves as a support base for the apparatus and the nursing baby bottle when the support bushing is inserted into the open end of the shell body. The ram moves along a rectilinear path in the axial direction when a force is exerted on the handle by a user urging the handle towards the bushing and the lower end of the shell body thereby compressing the flexible liner and reducing its volume so that any air trapped in the liner is expelled through the nipple. When the apparatus and baby nursing bottle are set aside, particularly in upright position and resting on the handle, the weight of the liquid in the flexible liner presses down upon the ram causing the liquid within the liner to be in a slightly compressed state thereby filling the nipple to prevent air from reentering the nipple.

The invention further resides in a method of utilizing the apparatus with a flexible liner baby nursing bottle and includes insertion of the support bushing coaxially into the lower open end portion of the shell body of the flexible liner nursing bottle wherein the ram portion is located within the shell body in the region of the bottom portion of the flexible liner. A user exerts a force on the handle portion urging the ram into contact with the flexible liner to reduce its volume and expel any air within the cavity formed by the liner and the nipple through the nipple. Upon interruption of the nursing process, the apparatus and flexible liner nursing bottle are placed in an upright position with the support portion of the handle in contact with a resting surface. The ram portion is maintained in contact with the flexible liner so that the weight of the liquid contents is supported thereby maintaining the volume of the flexible liner in a reduced condition to prevent air from reentering through the nipple.

BRIEF DESCRIPTION OF THE DRAWINGS

Other features and advantages of the present invention will become readily apparent from the following written description and drawings wherein:

FIG. 1 illustrates apparatus embodying the present invention as it may be used with a flexible liner baby nursing bottle;

FIG. 2 is a perspective illustration showing the apparatus of the present invention in another embodiment.

DETAILED DESCRIPTION OF THE PREFERRED EMBODIMENTS

Turning now to the drawings and considering the invention in further detail, a flexible liner baby nursing body is illustrated in FIG. 1 and generally indicated 10. The nursing bottle 10 includes a cylindrically shaped shell body 12 having an open upper end portion 14 and a lower open end portion 16. A flexible, sack-like liner 18 is inserted into the upper end portion 14 and is supported on the shell body 12 by overlapping the open end portion of the liner over the upper circumferential edge 20 of the shell body. The overlapped liner 18 is secured to the shell body 12 by means of a nipple 22 which has a lower circumferential flange portion 24 arranged for complementary engagement with an annular receiving channel 26 located in the outer surface 28 of the shell body 12 to pinch the liner between the nipple and the shell body outer wall. The shell body 12 and liner 18 are typically well known as is the nipple 22 which includes an orifice 30 through which a liquid L, such as formula or the like, is sucked through by an infant being nursed.

The apparatus of the present invention is generally designated 32 and includes an annulus shaped support bushing 34 which has the general shape of the lower open end portion 16 of the shell body 12 and is radially slightly larger than the size of the open end such that the peripheral wall 36 of the support bushing 34 will be frictionally engaged with the inner wall surface of the shell body 12 to couple the apparatus to the nursing bottle. As illustrated, the peripheral wall 36 of the support bushing 34 has a slight upward taper giving it a wedge like shape to permit ease of insertion into the lower end portion 16 of the shell body 12. The support bushing 34 also includes an opening 40 extending axially through the support bushing 34 between the upper surface 42 and lower surface 44. An axially elongated connecting rod 46 extends through the opening 40 and includes a disk shaped ram 48 at one end 50 of the connecting rod. The disk shaped ram has diameter slightly smaller than the inner diameter of the shell body 12 to permit the ram 48 to move axially with the connecting rod 46 as it moves along a rectilinear path indicated by arrow 52.

A disk shaped handle 54 is connected to the end 56 opposite the end 50 of the connecting rod 46. The size of the handle 54 is such that it defines a support surface 58 so that the apparatus 32 and nursing bottle 10 may be held in an upright position on a resting surface S of a table top or the like.

As illustrated in FIG. 1, a user fills the flexible liner 18 with a liquid L and next applies the nipple 22 to engage the liner and nipple to the shell body 12. The liner 18 is generally fully extended inwardly into the shell body 12. The ram portion 48 of the apparatus 32 is shown in phantom and at position A. A user then pushes on the handle 54 which urges the ram 48 into contact with the flexible liner 18 and forces liquid into the inner cavity 23 of the nipple 22 forcing air through the orifice 30 and filling the inner chamber 23 with liquid. As the infant nurses, the volume of the liquid in the flexible liner 18 decreases and at some time during the nursing process, the nursing bottle and apparatus are set aside to attend to burping the infant. As illustrated in FIG. 1, the apparatus and baby bottle are set aside in an upright position with the supporting surface 58 of the handle 54 resting on the surface S of a table and the like. The weight of the liquid L in the liner 18 rests on the surface of the ram portion 48 and since there is less liquid in the liner 18, the ram urges the bottom portion of the liner upward away from the lower portion of the shell body 12 and is illustrated as position B. It can be seen that the volume of the flexible liner 18 is reduced to accommodate the volume of liquid L left in the bottle and maintains the liquid in a compressive state in the inner chamber 23 of the nipple 22 to prevent air from reentering through the orifice 30 of the nipple. As the process continues it can be seen in FIG. 1 that the ram 48 is further extended into the shell of the body thereby reducing the volume of the flexible liner 18 and as illustrated at position C, maintains the liquid in the inner chamber 23 of the nipple 22 to prevent reentry of air.

The length of the connecting rod 46 within the shell body 12 is preferably at least as long as the axial length of the shell body. The apparatus is also preferably made of plastic or other non-toxic material. In addition, the construction of the apparatus is such that all edges are rounded to eliminate any sharpness and prevent puncture of the liner and/or injury to the user or infant.

Turning to FIG. 2, an alternate embodiment of the apparatus embodying the present invention is illustrated therein and generally designated 60. The apparatus 60 includes a connecting rod 62 having a disk shaped ram portion 64 at one end 66 and a disk shaped handle portion 68 located at the opposite end 70 of the connecting rod 62. The connecting rod 62 passes through and is guided by a support bushing generally indicated 72 and which comprises generally a cylindrically body 74 having an upper portion 76 having a generally tapered peripheral edge 78 continuous to and integral with a peripheral wall 80. An annular flange 82 forms a lower portion of the body 74 generally indicated 84. The bushing 72 includes an axial opening 86 extending completely through the body 74 between a lower surface 88 and an upper surface 90. The central axial opening 86 is slightly larger than the diameter of the connecting rod 62 to permit the connecting rod to move freely but with minimal lateral movement through the body.

The shape of the support bushing body 74 is such that it approximates the shape of the lower open end portion of the shell body of the flexible liner baby nursing bottle. The diameter of the body portion 74 is slightly larger than the diameter of the lower open end portion of the shell body so that the support bushing will be frictionally engaged with the inner wall of the shell to maintain the apparatus 60 in engagement with the baby nursing bottle. The peripheral wall 80 of the support bushing 72 may be roughened or serrated to provide additional frictional engaging properties.

In operation, the tapered peripheral edge 78 aids in guiding the support bushing 72 into the lower open end portion of the shell body. The support bushing 72 is inserted axially into the shell body until the flange 82 comes in contact with the shell body.

A method and apparatus for expelling air from a flexible liner baby nursing bottle has been disclosed above in several preferred embodiments. It will be recognized that numerous changes and substitutions may be made, for example, to the size and shape of the ram portion and handle portions and the configuration of the support bushing without departing from the spirit and scope of the invention and therefore the invention has been disclosed by way of illustration rather than limitation.

The invention claimed is:

1. In combination with a nursing baby bottle of the general type having a generally cylindrical shell body characterized by an open upper end portion for receiving and supporting a sack-like, flexible liner which contains a liquid to be dispensed, a nipple for covering the open upper end portion of the shell and liner, the liner extending generally axially inward into the shell body and toward an open lower end portion of the shell body, apparatus for varying the volume of the flexible liner as the liquid is dispensed, said apparatus comprising:

an axially elongated connecting rod having first and second ends;

support means comprising a body having a thickness, a first and second circumferential surface disposed opposite one another and a peripheral size and shape generally corresponding to the size and shape of the lower open end portion of the shell body for insertion therein and for complementary frictional engagement with the lower open end portion of the shell body, said support means body having an aperture extending axially through said body between said first and second circumferential surfaces, said aperture being dimensioned for carrying and guiding said connecting rod in an axial direction along a rectilinear path and for limiting lateral movement of said connecting rod with respect to the shell body;

means coupled to one end of said connecting rod and defining a ram, said ram being dimensioned smaller than the cross-sectional dimension of the shell body to permit the ram to be received within the shell body without contacting the shell body;

means coupled to the other end of said connecting rod and defining a handle, said support means being intermediate said handle and said ram, said handle further having means for supporting said apparatus and baby nursing bottle in an axially upright position on a resting surface;

said ram being continuously movable along said rectilinear path in both a direction away from and toward the open upward end of the shell body and out of and into contact with the flexible liner to vary the volume of the liner to expel air from the liner so that the volume of the liner is substantially equal to the volume of the liquid contained in the liner and to prevent reentry of air into the liner through the nipple when the apparatus and baby nursing bottle is supported on the resting surface in an upright position by said handle support means.

2. Apparatus according to claim 1 wherein said ram is disk shaped.

3. Apparatus according to claim 1 wherein said handle is disk shaped.

4. Apparatus according to claim 1 wherein said support means body is an annular bushing and further comprises an increasing tapered peripheral wall portion extending generally in a direction from one of said first and second circumferential surfaces toward the other of said first and second circumferential surfaces and a flanged end portion being located at the larger diameter of said one and other of said first and second circumferential surfaces, said flanged end portion defining means for limiting the distance said support means body is inserted into said lower open end portion of the shell body.

5. Apparatus according to claim 4 wherein said peripheral wall portion of said support means body is roughened.

6. Method for eliminating air from a nursing baby bottle of the general type having a flexible liner for holding liquid which is to be dispensed, a nipple and a shell body for supporting the flexible liner and the nipple, the body supporting the nipple at one end and having an opening at the other end, said method comprising the steps of:

providing a connecting rod having a first end portion including plunger means and a second end portion including base supporting means;

providing a shell body supporting means for supporting the connecting rod with reference to the shell body and having an axial opening dimensioned to pass the connecting rod through the opening;

attaching the shell body supporting means to the shell body with the first end portion of the connecting rod extending along the longitudinal axis within the shell body and adjacent to the flexible liner;

applying a force to the second end portion of the connecting rod thereby moving the connecting rod and causing the first end portion to contact and apply force to the flexible liner reducing its volume and being applied until all of the air within the liner is expelled with only liquid remaining, and resting the weight of the assembled combination of the connecting rod, supporting means and nursing baby bottle on the second end portion of the connecting rod thus resulting in the first end portion applying a constant force to the flexible liner and preventing air from reentering the flexible liner.

7. Method for eliminating air as defined in claim 6 wherein the step of providing a connecting rod includes providing a disk shaped first end portion defining said plunger means and a disk shaped second end portion defining said base supporting means.

* * * * *